US005905140A

United States Patent [19]

Hansen

[11] Patent Number: 5,905,140

[45] Date of Patent: May 18, 1999

[54] SELECTIVE ACYLATION METHOD

[75] Inventor: Louis Brammer Hansen, Værløse, Denmark

[73] Assignee: Novo Nordisk A/S, Novo Allé, Bagsvaerd, Denmark

[21] Appl. No.: 08/889,262

[22] Filed: Jul. 8, 1997

Related U.S. Application Data

[60] Provisional application No. 60/021,653, Jul. 12, 1996.

[30] Foreign Application Priority Data

Jul. 11, 1996 [DK] Denmark ................................ 0778/96

[51] Int. Cl.$^{6}$ .............................. A61K 38/28; C07K 1/00

[52] U.S. Cl. ......................... 530/303; 530/324; 530/345; 530/402; 514/3

[58] Field of Search .................................... 530/303, 324, 530/345, 402; 514/3

[56] References Cited

U.S. PATENT DOCUMENTS

| | | | |
|---|---|---|---|
| 3,869,437 | 3/1975 | Lindsay et al. | 530/363 |
| 4,369,179 | 1/1983 | Rink et al. | 424/177 |
| 5,304,473 | 4/1994 | Belagaje et al. | 435/69.7 |
| 5,646,242 | 7/1997 | Baker et al. | 530/303 |

FOREIGN PATENT DOCUMENTS

| | | |
|---|---|---|
| 0 712 861 A2 | 5/1996 | European Pat. Off. . |
| 0 712 862 A2 | 5/1996 | European Pat. Off. . |
| WO 95/07931 | 3/1995 | WIPO . |

OTHER PUBLICATIONS

Diaglog Information Services, Abstract 351, Accession No. 008078156, JP, A, 1254699.

*Primary Examiner*—Cecilia J. Tsang
*Assistant Examiner*—Abdel A. Mohamed
*Attorney, Agent, or Firm*—Steve T. Zelson, Esq.; Reza Green, Esq.

[57] ABSTRACT

A method of selectively acylating an insulin, an insulin analogue or a precursor thereof having a free ϵ-amino group of a Lys residue contained therein and at least one free α-amino group which method comprises reacting the ϵ-amino group with an activated amide in a polar solvent in the presence of a base.

31 Claims, No Drawings

SELECTIVE ACYLATION METHOD

CROSS-REFERENCE TO RELATED APPLICATIONS

This application claims priority under 35 U.S.C. 119 of U.S. provisional application Ser. No. 60/021,653, filed on Jul. 12, 1996 and Danish application Ser. No. 0778/96 filed Jul. 11, 1996, the contents of which are fully incorporated herein by reference.

FIELD OF THE INVENTION

The present invention relates to a method of introducing an acyl group into a peptide. More particularly, the invention relates to an improved method of acylating the ε-amino group of a lysine residue contained in a naturally occurring insulin or an analogue or a precursor thereof.

BACKGROUND OF THE INVENTION

Human insulin and closely related insulins have three primary amino groups in the molecule namely the α-amino groups of $Gly^{A1}$ and $Phe^{B1}$, respectively, and the ε-amino group of $Lys^{B29}$. N-Acylation of an unprotected insulin may—depending on the conditions—lead to a complex mixture of mono-, di- and even triacylated products. However, although a certain preference for acylation of a specific position can often be observed the preference is not always sufficiently pronounced to make such direct acylation useful as a method of producing monoacylated insulins since the formation of the desired product may be accompanied by the formation of considerable amounts of closely related by-products. When by-products are formed, this happens at the expense of the desired product and may lead to problems in the purification of the desired product.

Acylation of only one or two specific amino groups in the insulin molecule can be achieved if a suitably protected intermediate is available. A suitable intermediate can be an insulin derivative in which the amino group(s) not to be acylated is (are) blocked with a protection group which can be removed selectively after the acylation has been performed. Such a protected intermediate can either be an insulin precursor or an insulin derivative in which it has been possible to introduce one or two protection groups in a specific way. For economic reasons, it is very attractive to avoid the use of specific of protection groups if possible.

Friesen HJ et aL (Semisynthetic Peptides and Proteins (Offord RE, DiBello C, eds.) 161–179, 1978, London) describe acylation of insulin with N-hydroxysuccinimide esters (in the following referred to as ONSu-esters) and other activated esters under various conditions, as summarised in tables 4 and 5 l.c. A certain selectivity is seen but invariably A1 monosubstituted and B29 monosubstituted products are obtained in mixtures with each other and with disubstituted products. The highest total yield of monosubstituted products reported is 75% but of this 85% was the A1 isomer. In other cases the total yield of monosubstituted products were in the range 45–55% of which 70–72% was the ε-B29 isomer.

As demonstrated by Friesen HJ et al. (in: Chemistry, Structure and Function of Insulin and Related Hormones, Proceedings of the Second International Insulin Symposium (Brandenburg D, Wollmer A, eds.), New York, 1980), the pH of the reaction medium has a very strong influence on the course of the reaction when insulin is acylated with ONSu-esters or certain other acylating agents. Thus, at pH 5–6 monoacylation preferably takes place in the B1 amino group and diacylated product will preferably be A1, B1-diacylated insulin. At pH 6.8–9.2 monoacylation preferably takes place in the A1 amino group while diacylated product can be either A1, B1- or A1, ε-B29-diacylated insulin. Finally, at pH above 10 monoacylation preferably takes place in the ε-amino group of $Lys^{B29}$ while a further acyl group preferably goes to the amino group of A1.

A method which enables selective acylation of proinsulin, insulin or an insulin analogue having a free ε-amino group is disclosed in EP 0 712 861 A2 and EP 0 712 862 A2 (both Eli Lilly and Company). According to the method, unprotected insulins are acylated with soluble, activated fatty acid esters, in particular ONSu-esters, under basic conditions in a polar solvent.

EP 0 511 600 A2 (Kuraray Co., Ltd.) relates i.a. to protein derivatives of the formula $[protein][Z]_n$ wherein [protein] represents a protein having a number of amino groups, [Z] is a residue represented by the formula —CO—W—COOH wherein W is a divalent long chain hydrocarbon group which may also contain certain hetero atoms and n represents an average of the number of amide bonds between [Z] and [protein]. The derivatives are prepared by reaction between the parent protein and a long chain carboxylic acid imide ester in an aqueous solution of a salt optionally also containing an organic solvent. No specificity of the acylation is mentioned and the fact that n is stated to be an average number seems to indicate that no specificity is achieved. It is mentioned, that insulin is one of the proteins from which derivatives according to the invention can be made, but no specific insulin derivative is disclosed in EP 0 511 600 nor is there any indication of a preferred [Z] or a preferred position in which [Z] should be introduced in order to obtain a useful insulin derivative.

Examples of insulin derivatives, acylated in the ε-amino group of the Lys residue contained therein, are described in WO 95/07931 (NOVO NORDISK A/S). The derivatives can be produced by acylation of the corresponding (A1, B1)-diBoc insulin, prepared from the corresponding insulin by reaction e.g. with di-tert-butyl dicarbonate and subsequently removing the protection groups and by acylation of a single chain insulin precursor which subsequently has to be processed further. Surprisingly, it has now been found that high yields of insulins, monoacylated in the ε-amino group of a Lys residue contained therein, can be obtained by the method of the present invention.

SUMMARY OF THE INVENTION

In its broadest aspect, the present invention relates to a method of selectively acylating an insulin, an insulin analogue or a precursor thereof having a free ε-amino group of a Lys residue contained therein and at least one free α-amino group which method comprises reacting the ε-amino group with an activated amide in a polar solvent in the presence of a base.

DETAILED DESCRIPTION OF THE INVENTION

In a preferred embodiment, the parent insulin (i.e. the naturally occurring insulin, insulin analogue or insulin precursor to be acylated using the method according to the invention) is des(B30) human insulin. Examples of other preferred parent insulins are human insulin, porcine insulin and other naturally occurring insulins and also insulin analogues or insulin precursors in which at least one Lys having a free ε-amino group and an amino acid residue having a free α-amino group is present.

One particularly preferred group of parent insulins are insulin analogues in which the amino acid residue in position B1 has been deleted.

Another particularly preferred group of parent insulins are insulin analogues which have Lys in position B28 and Pro in position B29. A preferred example from this group is $Lys^{B28}Pro^{B29}$ human insulin.

Another particularly preferred group of parent insulins are insulin analogues which have Asp in position B28. A preferred example from this group is $Asp^{B28}$ human insulin.

Other particularly preferred groups of parent insulins are insulin analogues in which in which the A-chain and/or the B-chain have an N-terminal extension and insulin analogues in which the A-chain and/or the B-chain have a C-terminal extension.

Further insulin analogues which can be useful as parent insulins in the method of the present invention are such in which one or more of the amino acid residues, preferably one, two or three of them, has been substituted by another codable amino acid residue. Thus, in position A21 a parent insulin may in stead of Asn have an amino acid residue selected from the group comprising Ala, Gin, Glu, Gly, His, Ile, Leu, Met, Ser, Thr, Trp, Tyr or Val, in particular an amino acid residue selected from the group comprising Gly, Ala, Ser and Thr. Insulin analogues useful as parent insulins in the method of the present invention may also be modified by a combination of the changes outlined above.

By "insulin analogue" as used herein is meant a peptide having a molecular structure similar to that of human insulin including the disulphide bridges between $Cys^{A7}$ and $Cys^{B7}$ and between $Cys^{A20}$ and $Cys^{B19}$ and an internal disulphide bridge between $Cys^{A6}$ and $Cys^{A11}$, and which has insulin activity. When the amino acid at position B1 is deleted, the position of the remaining amino acids of the B-chain are not renumbered.

The expression "a codable amino acid residue" as used herein designates an amino acid residue which can be coded for by the genetic code, i.e. a triplet ("codon") of nucleotides.

The preferred parent insulin analogue des(B30) human insulin can be prepared by several methods, i.a. by enzymatic hydrolysis of human insulin, porcine insulin and insulin derivatives. Enzymes that facilitate this hydrolysis are lysyl endopeptidases, such as trypsin and Achromobacter lyticus proteases. Furthermore, des(B30) human insulin can be prepared in an enzymatic process from a single chain insulin precursor of the formula B(1–29)-Ala-Ala-Lys-A(1–21) wherein B(1–29) designates the amino acid sequence from position 1 to position 29 of the B-chain of human insulin and A(1–21) designates the amino acid sequence from position 1 to position 21 of the A-chain of human insulin. This precursor can be obtained as described in EP 163.529. A suitable enzyme for the process is Achromobacter lyticus protease 1, EC code No. 3.4.21.50. The enzyme can be used in a soluble form, or immobilised on a N-hydroxysuccinimide activated Sepharose. After completion of the reaction, the des(B30) human insulin formed can be isolated in a number of ways, i.a. by precipitation by addition of zinc or sodium salts.

The acylation reaction is usually carried out with a concentration of the parent insulin of from about 0.1% w/w to about 25% w/w, preferably from about 2% w/w to about 12% w/w, more preferred from about 3% w/w to about 8% w/w at the beginning of the reaction.

In one preferred embodiment of the invention, the acyl group to be introduced into the ε-amino group of a Lys residue is the acyl group of a monocarboxylic acid of the general formula (I):

$$M\text{—}COOH \quad \text{(I)}$$

wherein M is a long chain hydrocarbon group which may optionally be interrupted by one or more groups each independently selected from the group consisting of an oxygen atom and a sulphur atom. More preferred, the acyl group is the acyl group of an unbranched, aliphatic monocarboxylic acid having from 6 to 24 carbon atoms, in particular an acyl group selected from the group comprising $CH_3(CH_2)_8CO$—, $CH_3(CH_2)_9CO$—, $CH_3(CH_2)_{10}CO$—, $CH_3(CH_2)_{11}CO$—, $CH_3(CH_2)_{12}CO$—, $CH_3(CH_2)_{13}CO$—, $CH_3(CH_2)_{14}CO$—, $CH_3(CH_2)_{11}CO$—, $CH_3(CH_2)17CO$—, $CH_3(CH_2)_{18}CO$—, $CH_3(CH_2)_{19}CO$—, $CH_3(CH_2)_{20}CO$—, $CH_3(CH_2)_{21}CO$— and $CH_3(CH_2)_{22}CO$—.

In another preferred embodiment of the invention, the acyl group to be introduced into the ε-mino group of a Lys residue is one of the acyl groups of a dicarboxylic acid of the general formula (II):

$$HOOC\text{—}D\text{—}COOH \quad \text{(II)}$$

wherein D is a long chain hydrocarbon group which may optionally be interrupted by one or more groups each independently selected from the group consisting of an oxygen atom and a sulphur atom. More preferred, the acyl group is one of the acyl groups of a dicarboxylic acid of the general formula (II) wherein D is an unbranched, divalent aliphatic hydrocarbon group having from 6 to 22 carbon atoms, in particular an acyl group selected from the group comprising $HOOC(CH_2)_6CO$—, $HOOC(CH_2)_8CO$—, $HOOC(CH_2)_{10}CO$—, $HOOC(CH_2)_{12}CO$—, $HOOC(CH_2)_{14}CO$—, $HOOC(CH_2)_{16}CO$—, $HOOC(CH_2)_{18}CO$—, $HOOC(CH_2)_{20}CO$— and $HOOC(CH_2)_{22}CO$—.

In further preferred embodiment of the invention, the acyl group to be introduced into the ε-amino group of a Lys residue is a group of the general formula (III):

$$CH_3(CH_2)_xCONHCH(COOR^1)CH_2CH_2CO\text{—} \quad \text{(III)}$$

wherein x is an integer from 8 to 24 and $R^1$ is hydrogen or a group which can be exchanged with hydrogen after the acylation has been performed, for example methyl, ethyl or tert-butyl. Preferred values of x are 10, 12 and 14. When the acylation has been performed and $R^1$ is different from hydrogen, the ester group of which $R^1$ is a part can be hydrolysed to give the corresponding free acid and the alcohol $R^1OH$ by methods known per se. Thus, when $R^1$ is methyl or ethyl, the hydrolysis can be performed under alkaline conditions and when $R^1$ is tert-butyl, the hydrolysis can be carried out using trifluoroacetic acid.

In further preferred embodiment of the invention, the acyl group to be introduced into the ε-amino group of a Lys residue is a group of the general formula (IV):

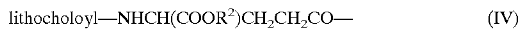

$$\text{lithocholoyl—}NHCH(COOR^2)CH_2CH_2CO\text{—} \quad \text{(IV)}$$

wherein $R^2$ is hydrogen or a group which can be exchanged with hydrogen after the acylation has been performed, for example methyl, ethyl or tert-butyl. When the acylation has been performed and $R^2$ is different from hydrogen, the ester group of which $R^2$ is a part can be hydrolysed to give the corresponding free acid and the alcohol $R^2OH$ by methods known per se. Thus, when $R^2$ is methyl or ethyl, the hydrolysis can be performed under alkaline conditions and when $R^2$ is teft-butyl, the hydrolysis can be carried out using trifluoroacetic acid.

The acylation of the parent insulin is carried out using an acylating agent which is an activated amide, more particularly an azolide of the acid corresponding to the acyl group to be introduced. Such azolides (1-acylazoles) can be prepared according to known methods, see for example Staab HA *Angew. Chem.* 74 (1962) 407–423. Examples of azloes which can be used in the preparation of the acylating agents of this invention are pyrazole, imidazole, 1,2,3-triazole, 1,2,4-triazole, tetrazole, phenyltetrazole and-where possible-the corresponding benzanelated compounds e.g. 1H-indazol, benzimidazole and benzotriazole. Preferred azoles for the preparation of the acylating agent are 1,2,4-triazole, benzotriazole and substituted benzotriazoles. Optionally, the azoles mentioned can be substituted with one or more substituents selected from the group comprising alkyl ($C_1$–$C_5$, branched or unbranched, in particular methyl, ethyl, propyl and isopropyl), halogen (e.g. fluoro, chloro and bromo, in particular fluoro and chloro), nitro, alkoxy ($C_1$–$C_5$, branched or unbranched, in particular methoxy, ethoxy, propoxy and isopropoxy), dialkylated amino ($C_1$–$C_5$, branched or unbranched), sulphonic acid, carboxy and alkoxycarbonyl ($C_1$–$C_5$, branched or unbranched). A preferred group of acylating agents are 1-acyl benzotriazoles and a preferred acylating agent is 1-tetradecanoyl benzotriazole. Other preferred 1-acyl benzotriazoles are such which are derived from mono- or disubstituted benzotriazoles, e.g. 5-substituted or 6-substituted or 5,6-disubstituted benzotriazoles such as 5-methylbenzotriazole, 5-chlorobenzotriazole, 6-chlorobenzotriazole, 5-nitrobenzotriazole, 5,6-dimethylbenzotriazole and 5,6-dichlorobenzotriazole.

The acylation is carried out in a polar solvent which can be a mixture of water and at least one water-miscible organic solvent. Examples of water-miscible solvents which may be useful either alone or in mixtures are lower alcohols, e.g. methanol, ethanol and 2-propanol, lower straight chain and branched ketones, e.g. acetone, cyclic ethers, e.g. tetrahydrofuran and dioxane, straight chain and cyclic amides, e.g. dimethylformamide, dimethylacetamide and N-methyl-2-pyrrolidone, nitriles e.g. acetonitrile and sulfoxides, e.g. dimethyl sulfoxide. Most preferred among the water-miscible organic solvents are N-methyl-2-pyrrolidone, dimethylformamide, dimethylacetamide and dimethyl sulfoxide.

The amount of water in the reaction medium may vary within a broad range so that the medium in general contains from about 1% w/w to about 99% w/w of water. When N-methyl-2-pyrrolidone is used as the water-miscible organic solvent the amount of water in the medium is preferably from about 1% w/w to about 90% w/w, more preferred from about 10% w/w or about 20% w/w to about 75% w/w.

The acylation is carried out in the presence of an excess of a medium strong or strong base which can be either an inorganic base or an organic base. Examples of inorganic bases are sodium hydroxide, potassium hydroxide, sodium carbonate and potassium carbonate. Examples of organic bases are tertiary amines, e.g. ethyidiisopropylamine, triethylamine and diethylethanolamine. Preferably, an organic base is used. The amount of base used is generally in excess of 5 mol per mol of parent insulin, e.g. 10 to 30 mol or even 100 mol of base per mol of parent insulin.

Basically, the lower limit of the temperature at which the acylation can be carried out is determined by the freezing point of the medium while the upper limit is determined by the temperature at which the parent insulin or the acylated insulin will deteriorate. This again will depend i.a. on the composition of the medium. Thus, while it may be possible to carry out the reaction at temperatures between −30° C. and 70° C. it is usually most convenient to carry out the reaction at a temperature between about −5° C. and about 30° C.

Isolation and purification of the products prepared by the method of the present invention can be carried out by methods known per se, including gel filtration and chromatography.

The present invention is further illustrated by the following examples which, however, are not to be construed as limiting the scope of protection. The features disclosed in the foregoing description and in the following examples may, either separately or in any combination thereof, be material for realizing the invention in diverse forms thereof.

EXAMPLES

Analytical

The reaction mixtures—except in Example 4—were analysed by RP-HPLC as described below using a Merck/Hitachi apparatus equipped with a Diode Array Detector.

Column: 4.0×125 mm, operated at 60°.

Column material: dimethyl butyl dimethyl silyl substituted 100 Å, 5 mm silica.

Eluent gradient system:

Eluent A: acetonitrile (7.8%) in water containing ammonium sulphate (2.0%) at pH 2.5.

Eluent B: acetonitrile (53.9%) in water.

Flow rate: 1.0 ml/min.

Detection: UV absorption at 280 nm.

Cycle time: 65 min.

The yields stated are based on the area of the peaks in the chromatograms.

The identity of the acylated insulins was determined by their retention time in RP-HPLC and by isolation and mass spectrometry/peptide mapping performed on the acylated products 1) without any pre-treatment, 2) after pre-treatment with dithiotreitol for reduction of the disulphide bonds and 3) after pre-treatment with dithiotreitol and Staphylococcus aureus protease V8 for cleavage of the B-chain between position 21 and position 22.

Preparation of starting materials:

Example 1

Preparation of 1-tetradecanoylbenzotriazole.

Benzotriazole (59.6 g, 0.50 mol) was dissolved in tert-butyl methyl ether (950 ml) at 20° and triethylamine (50.6 g, 0.50 mol) was added. Tetradecanoyl chloride (125.0 g, 0.51 mol) was added over a period of 30 min, the temperature being kept at 20–30° C. by cooling. The resulting precipitate was removed by filtration, and the filtrate evaporated to dryness under reduced pressure at 60° C. The residue was dissolved in acetone (375 ml) at 60° C. After cooling to 0° C., the resulting crystals were isolated by filtration, washed with acetone (120 ml) and dried to constant weight under reduced pressure at 20° C.

Yield: 142.3 g (86%) of white crystalline 1-tetradecanoylbenzotriazole, melting at 58.0° C. (peak value) determined by Differential Scanning Calorimetry (DSC).

Under similar reaction conditions, the following acylated triazoles were also prepared:

1-tetradecanoyl-1,2,4-triazole, DSC: 59.7° C. (recryst. from tetrahydrofuran), 5-methyl-1-tetradecanoylbenzotriazole, DSC: 69.5° C. (recryst. from 2-propanol), 5-chloro-1-tetradecanoylbenzotriazole (NMR data seem to indicate that the product also contained some 6-chloro-1-tetradecanoylbenzotriazole), DSC: 52.1° C. (recryst. from 2-propanol), 5-nitro-1-tetradecanoylbenzotriazole, DSC: 117.5° C. (recryst. from acetone), 5,6-dichloro-1-tetradecanoybenzotriazole, DSC: 60.6° C. (recryst. from tetrahydrofuran), 5,6-dimethyl-1-tetradecanoylbenzotriazole, DSC: 61.6° C. (recryst. from acetone), 1-dodecanoylbenzotriazole, DSC: 43.9° C. (recryst. from n-heptane) and 1-hexadecanoylbenzotriazole, DSC 62.4° C. (recryst. from tert-butyl acetate).

Example 2

Preparation of 1-(19-carboxynonadecanoyl) benzotriazole.

A solution of eicosanedioic acid (3.43 g, 10.0 mmol), dicyclohexylcarbodimide (2.06 g, 10.0 mmol), benzotriazole (1.19 g, 10.0 mmol) and dimethylamino-pyridine hydrochloride in anhydrous tetrahydrofuran (200 ml) was stirred for two days at room temperature. The resulting suspension was filtered, and the filtrate evaporated to dryness under reduced pressure. The residue was suspended in dichloromethane (100 ml), and undissolved material was isolated by filtration. The dried filter cake (2.0 g) was recrystallised from acetone (200 ml) yielding 0.70 g (16%) of white crystalline 1-(19-carboxynonadecanoyl)benzotriazole, melting at 111.9° C. (DSC peak value).

Example 3

Preparation of 1-(17-carboxyheptadecanoyl) benzotriazole.

Under similar reaction conditions as in Example 2, but using octadecanedioic acid in stead of eicosanedioic acid, 1-(17-carboxyheptadecanoyl)-benzotriazole was prepared. The compound had a melting point of 105.2° C. (DSC peak value).

Example 4

Preparation of des(B30) human insulin from a single chain insulin precursor.

Single chain insulin precursor of the formula B(1–29)-Ala-Ala-Lys-A(1–21) wherein B(1–29) designates the amino acid sequence from position 1 to position 29 of the B-chain of human insulin and A(1–21) designates the amino acid sequence from position 1 to position 21 of the A-chain of human insulin was obtained as described in EP 163.529.

5 g of wet salt cake containing about 1.5 g of the above-mentioned single chain precursor was dissolved in 25 mM sodium hydrogen carbonate (350 ml) at room temperature. The pH value of the solution was adjusted to 9.0 by addition of 1.0M sodium hydroxide (1 ml). Achromobacter lyticus protease 1, immobilised on N-hydroxysuccinimide activated Sepharose (10 ml of gel with an enzyme density of approximately 1.0 mg/l) was added. The reaction mixture was stirred for 23 hours at room temperature and the immobilised enzyme was then removed by filtration. The filtrate was analysed by RP-HPLC as described below.

Based on the area of the peaks in the chromatogram, the relative amount of des(B30) human insulin found in the reaction mixture was 95.2% (retention time: 27.7 min) and the relative amount of starting material was 0.1% (retention time: 15.0 min).

Analytical

The reaction mixture was analysed by RP-HPLC on equipment supplied by Waters.

Column: 4.0×250 mm, operated at 50°.

Column material: YMC 120 A, 5 my OdDMe silylated silica gel.

Eluent gradient system:

Eluent A: 0.20M sodium sulphate, 0.04M phosphoric acid in acetonitrile (10%) in water, pH 2.3.

Eluent B: acetonitrile (50%) in water.

Run time: 60 minutes

Flow rate: 1.0 ml/min

Detection: UV absorption at 214 nm

| | |
|---|---|
| gradient: | 00.00 min 64% A + 36% B |
| | 40.00 min 40% A + 60% B |
| | 41.00 min 64% A + 36% B |

Preparation of acylated insulins:

Example 5

Synthesis of $N^{\epsilon B29}$-tetradecanoyl des(B30) human insulin.

Des(B30) human insulin (0.50 g, assay: about 80%~0.070 mmol) was dissolved in N-methyl-2-pyrrolidone (7.0 ml) and water (3.5 ml) at 20° C. The solution was cooled to 0° C. Triethylamine (0.40 ml) was added. 1-Tetradecanoylbenzotriazole (1.50 ml of a 0.10M solution in N-methyl-2-pyrrolidone) was added over a period of 30 minutes. The turbid reaction mixture was stirred at 0° C. for 30 minutes, then at 20° C. for an additional 30 minutes.

The reaction mixture was analysed by RP-HPLC with the following results:

| Retention time, min | Compound | % yield |
|---|---|---|
| 11.00 | starting material | 7.3 |
| 25.20 | $N^{A1}$-tetradecanoyl des(B30) human insulin | 1.8 |
| 29.66 | $N^{\epsilon B29}$-tetradecanoyl des(B30) human insulin | 71.0 |
| 49.85 | Diacylated des(B30) human insulin | 7.7 |
| >50 | unknown products totalling | 10.4 |

Example 6

Synthesis of $N^{\epsilon B29}$-tetradecanoyl des(B30) human insulin.

Des(B30) human insulin (0.50 g, assay: about 66%~0.58 mmol) was dissolved in N-methyl-2-pyrrolidone (7.5 ml) and water (1.0 ml) at 20° C. Triethylamine (0.40 ml) was added. 1-Tetradecanoyl-1,2,4-triazole (1.0 ml of a 0.10M solution in N-methyl-2-pyrrolidone) was added in one portion. The homogenous reaction mixture was stirred at 20° C. for 10 minutes and then analysed by RP-HPLC with the following results:

| Retention time, min | Compound | % yield |
|---|---|---|
| 11.43 | starting material | 30.0 |
| 25.89 | $N^{A1}$-tetradecanoyl des(B30) human insulin | 8.4 |
| 30.37 | $N^{\epsilon B29}$-tetradecanoyl des(B30) human insulin | 43.5 |
| 50.20 | Diacylated des(B30) human insulin | 8.7 |
| >50.20 | unknown products totalling | 3.8 |

Example 7

Synthesis of $N^{\epsilon 29}$-tetradecanoyl des(B30) human insulin.

Des(B30) human insulin (0.50 g, assay: about 80%~0.070 mmol) was dissolved in dimethyl sulfoxide (7.0 ml) and water (3.5 ml) at 20° C. and triethylamine (0.40 ml) was added. 1-Tetradecanoylbenzotriazole (1.80 ml of a 0.10M solution in N-methyl-2-pyrrolidone) was added over a period of 2 minutes. The turbid reaction mixture was stirred at 20° C. for 90 minutes. The resulting homogeneous reaction mixture was analysed by RP-HPLC showing a yield of 59.4% $N^{\epsilon B29}$-tetradecanoyl des(B30) human insulin.

Example 8

Synthesis of $N^{\epsilon B29}$-tetradecanoyl des(B30) human insulin.

Des(B30) human insulin (0.50 g, assay: about 80%~0.070 mmol) was dissolved in dimethylformamide (7.0 ml) and 6M aqueous urea (2.0 ml) at 20° C. The solution was cooled to 0° C., and triethylamine (0.40 ml) was added. 1-Tetradecanoylbenzotriazole (1.10 ml of a 0.10M solution in N-methyl-2-pyrrolidone) was added in one portion. The turbid reaction mixture was stirred at 0° C. for 60 minutes. The resulting slightly turbid reaction mixture was analysed by RP-HPLC showing a yield of 74.2% $N^{\epsilon B29}$-tetradecanoyl des(B30) human insulin.

Example 9

Synthesis of $N^{\epsilon B29}$-tetradecanoyl des(B30) human insulin.

Des(B30) human insulin (0.50 g, assay: about 80%~0.070 mmol) was dissolved in N-methyl-2-pyrrolidone (7.0 ml) and water (2.0 ml) at 20° C. The solution was cooled to 0° C. Triethylamine (0.20 ml) was added. 1-Tetradecanoylbenzotriazole (1.00 ml of a 0.10M solution in N-methyl-2-pyrrolidone) was added in one portion. The turbid reaction mixture was stirred at 0° C. for 65 minutes. The resulting reaction mixture was analysed by RP-HPLC showing a yield of 68.3% $N^{\epsilon B29}$-tetradecanoyl des(B30) human insulin.

Example 10

Synthesis of $N^{\epsilon B29}$-tetradecanoyl des(B30) human insulin.

Des(B30) human insulin (0.50 g, assay: about 80%~0.070 mmol) was dissolved in N-methyl-2-pyrrolidone (7.0 ml) and 3M aqueous urea (3.5 ml) at 20° C. Ethyidiisopropylamine (0.50 ml) was added. 1-Tetradecanoylbenzotriazole (1.50 ml of a 0.10M solution in N-methyl-2-pyrrolidone) was added over a period of 2 minutes. The turbid reaction mixture was stirred at 20° C. for 90 minutes. The resulting reaction mixture was analysed by RP-HPLC showing a yield of 61.9% $N^{\epsilon B29}$-tetradecanoyl des(B30) human insulin.

Example 11

Synthesis of $N^{\epsilon B29}$-tetradecanoyl des(B30) human insulin.

Des(B30) human insulin (5.0 g, assay: about 34%~0.30 mmol) was dissolved in N-methyl-2-pyrrolidone (20.0 ml) at 20° C. After cooling to 0° C., triethylamine (1.50 ml) was added. 5-Nitro-1-tetradecanoylbenzotriazole (3.20 ml of a 0.10M solution in N-methyl-2-pyrrolidone) was added over a period of 10 minutes. The reaction mixture was stirred at 0° C. for 30 minutes. The resulting reaction mixture was analysed by RP-HPLC showing a yield of 58.3% $N^{\epsilon B29}$-tetradecanoyl des(B30) human insulin.

Example 12

Synthesis of $N^{\epsilon B29}$-tetradecanoyl des(B30) human insulin.

Des(B30) human insulin (5.0 g, assay: about 34%~0.30 mmol) was dissolved in N-methyl-2-pyrrolidone (20.0 ml) at 20° C. After cooling to 0° C. water (7.5 ml) and triethylamine (1.50 ml) was added. 5-Chloro-1-tetradecanoylbenzotriazole (4.5 ml of a 0.10M solution in N-methyl-2-pyrrolidone) was added over a period of 15 minutes. The turbid reaction mixture was stirred at 0° C. for 3 hours. The resulting reaction mixture was analysed by RP-HPLC showing a yield of 77.7% $N^{\epsilon B29}$-tetradecanoyl des(B30) human insulin.

Example 13

Synthesis of $N^{\epsilon B29}$-tetradecanoyl human insulin.

Human insulin (50 mg, 0.009 mmol) was dissolved in N-methyl-2-pyrrolidone (0.7 ml) and water (0.35 ml) at 0° C. Triethylamine (0.040 ml) was added. 1-Tetradecanoylbenzotriazole (0.150 ml of a 0.10M solution in N-methyl-2-pyrrolidone) was added in one portion. The turbid reaction mixture was stirred at 0° C. for 150 minutes. The resulting homogeneous reaction mixture was analysed by RP-HPLC showing a yield of 64.0% $N^{\epsilon B29}$-tetradecanoyl human insulin (retention time: 27.75 min).

Example 14

Synthesis of $N^{\epsilon B29}$-tetradecanoyl porcine insulin.

Porcine insulin (50 mg, 0.009 mmol) was dissolved in N-methyl-2-pyrrolidone (0.7 ml) and water (0.35 ml) at 0° C. Triethylamine (0.040 ml) was added. 1-Tetradecanoylbenzotriazole (0.150 ml of a 0.10M solution in N-methyl-2-pyrrolidone) was added in one portion. The turbid reaction mixture was stirred at 0° C. for 155 minutes. The resulting homogeneous reaction mixture was analysed by RP-HPLC showing a yield of 62.5% $N^{\epsilon B29}$-tetradecanoyl porcine insulin (retention time: 28.99 min).

Example 15

Synthesis of $N^{\epsilon B29}$-(19-carboxynonadecanoyl) des(B30) human insulin.

Des(B30) human insulin (5.0 g, assay: about 34%~0.30 mmol) was dissolved in N-methyl-2-pyrrolidone (30.0 ml) and water (6.9 ml) at 20° C. Triethylamine (1.10 ml) was added. 1-(19-carboxynonadecanoyl)benzotriazole (5.0 ml of a 0.10M solution in N-methyl-2-pyrrolidone) was added in one portion. The reaction mixture was stirred at 20° C. for 4.5 hours. The resulting reaction mixture was analysed by RP-HPLC showing a yield of 30.0% $N^{\epsilon B29}$-(19-carboxynonadecanoyl) des(B30) human insulin (retention time: 32.19 min). The amount of starting material was 57.3%.

Example 16

Synthesis of $N^{\epsilon B29}$-(17-carboxyheptadecanoyl) des(B30) human insulin.

Under similar reaction conditions as in Example 15, but using 1-(17-carboxyheptadecanoyl)benzotriazole in stead of 1-(19-carboxynonadecanoyl)benzotriazole, the resulting reaction mixture was analysed by RP-HPLC showing a yield of 24.9% $N^{\epsilon B29}$-(17-carboxyheptadecanoyl) des(B30) human insulin (retention time: 26.41 min). The amount of starting material was 68.3%.

Example 17

Synthesis of $N^{\epsilon B29}$-tetradecanoyl des(B30) human insulin.

Des(B30) human insulin (0.50 g, assay: about 80%~0.070 mmol) was dissolved in N-methyl-2-pyrrolidone (7.0 ml) and 3M aqueous urea (3.5 ml) at 20° C. Triethylamine (0.40 ml) was added, and the solution was cooled to −13° C. 1-Tetradecanoylbenzotriazole (1.80 ml of a 0.10M solution in N-methyl-2-pyrrolidone) was added in one portion. The resulting suspension was stirred at −13° C. for 47 hours. The reaction mixture was analysed by RP-HPLC showing a yield of 65.2% $N^{\epsilon B29}$-tetradecanoyl des(B30) human insulin.

Example 18

Synthesis of $N^{\epsilon B29}$-tetradecanoyl des(B30) human insulin.

Des(B30) human insulin (0.50 g, assay about 80%~0.070 mmol) was dissolved in N-methyl-2-pyrrolidone (7.0 ml) and water (2.0 ml) at 20° C. The solution was cooled to 0° C.

Triethylamine (0.40 ml) was added. 5-Methyl-1-tetradecanoylbenzotriazole (1.00 ml of a 0.10M solution in N-methyl-2-pyrrolidone) was added in one portion. The turbid reaction mixture was stirred at 0° C. for 2 hours. The resulting solution was analysed by RP-HPLC showing a yield of 66.8% $N^{\epsilon B29}$-tetradecanoyl des(B30) human insulin.

Example 19

Synthesis of $N^{\epsilon B29}$-tetradecanoyl des(B30) human insulin.

Des(B30) human insulin (0.50 g, assay about 80%~0.070 mmol) was dissolved in N-methyl-2-pyrrolidone (7.0 ml) and water (2.0 ml) at 20° C. Triethylamine (0.40 ml) was added. 5,6-Dichloro-1-tetradecanoylbenzotriazole (1.10 ml of a 0.10M solution in N-methyl-2-pyrrolidone) was added in one portion. The turbid reaction mixture was stirred at 20° C. for 1 hours. The resulting solution was analysed by RP-HPLC showing a yield of 68.8% $N^{\epsilon B29}$-tetradecanoyl des(B30) human insulin.

Example 20

Synthesis of $N^{\epsilon B29}$-tetradecanoyl des(B30) human insulin.

Des(B30) human insulin (5.0 g, assay about 30%~0.26 mmol) was dissolved in N-methyl-2-pyrrolidone (30.0 ml) and water (6.0 ml) at 20° C. Triethylamine (1.08 ml) was added. 5,6-Dimethyl-1-tetradecanoylbenzotriazole (4.00 ml of a 0.10M solution in N-methyl-2-pyrrolidone) was added over a period of 15 minutes. The turbid reaction mixture was stirred at 20° C. for 1 hours. The resulting solution was analysed by RP-HPLC showing a yield of 54.6% $N^{\epsilon B29}$-tetradecanoyl des(B30) human insulin.

Example 21

Synthesis of $N^{\epsilon B29}$-dodecanoyl des(B30) human insulin.

Des(B30) human insulin (0.10 g, assay about 80%~0.014 mmol) was dissolved in N-methyl-2-pyrrolidone (1.4 ml) and water (0.4 ml) at 20° C. The solution was cooled to 0° C. Triethylamine (0.08 ml) was added. 1-dodecanoylbenzotriazole (0.20 ml of a 0.10M solution in N-methyl-2-pyrrolidone) was added over a period of 3 minutes. The turbid reaction mixture was stirred at 0° C. for 40 minutes. The resulting solution was analysed by RP-HPLC showing a yield of 58.9% $N^{\epsilon B29}$-dodecanoyl des(B30) human insulin (retention time: 23.17 minutes), and 23.7% of starting material.

Example 22

Synthesis of $N^{\epsilon B29}$-hexadecanoyl des(B30) human insulin.

Des(B30) human insulin (0.10 g, assay about 80%~0.014 mmol) was dissolved in N-methyl-2-pyrrolidone (1.4 ml) and water (0.4 ml) at 20° C. The solution was cooled to 0° C. Triethylamine (0.08 ml) was added. 1-hexadecanoylbenzotriazole (0.20 ml of a 0.10M solution in N-methyl-2-pyrrolidone) was added over a period of 3 minutes. The turbid reaction mixture was stirred at 0° C. for 60 minutes. The still turbid reaction mixture was analysed by RP-HPLC showing a yield of 32.6% $N^{\epsilon B29}$-hexadecanoyl des(B30) human insulin (retention time: 33.41 minutes), and 59.2% of starting material.

I claim:

1. A method of selectively acylating an insulin, an insulin analogue or a precursor thereof having a free ε-amino group of a Lys residue contained therein and at least one free α-amino group, said method comprising reacting the insulin, insulin analogue, or precursor thereof with an activated aride in a polar solvent in the presence of a base, wherein the activated amide is a derivative of an acid corresponding to an acyl group to be introduced and wherein the ε-amino group is selectively acylated.

2. The method of claim 1 wherein the insulin is human insulin.

3. The method of claim 1 wherein the insulin is porcine insulin.

4. The method according to claim 1, wherein the solvent is selected from the group comprising N-methyl-2-pyrrolidone, dimethylformamide, dimethylacetamide and dimethyl sulfoxide.

5. The method according to claim 1, wherein the solvent contains from about 1% w/w to about 99% w/w of water.

6. The method according to claim 1, wherein the solvent is N-methyl-2-pyrrolidone containing from about 1% w/w to about 90% w/w.

7. The method of claim 1 wherein an insulin analogue is selectively acylated.

8. The method of claim 7 wherein the insulin analogue is des(B30) human insulin.

9. The method of claim 7 wherein the insulin analogue has Lys in position B28 and Pro in position B29.

10. The method of claim 7 wherein the insulin analogue is insulin in which $Phe^{B1}$ has been deleted.

11. The method of claim 7 wherein the insulin analogue is insulin in which the A-chain, the B-chain, or both the A-chain and B-chain have an N-terminal extension.

12. The method of claim 7 wherein the insulin is an insulin analogue in which the A-chain, the B-chain, or both the A-chain and B-chain have a C-terminal extension.

13. The method according to claim 1 wherein the acyl group to be introduced is the acyl group of a monocarboxylic acid of the general formula:

M—COOH (I)

wherein M is a long chain hydrocarbon group.

14. The method of claim 13 wherein the acyl group to be introduced is the acyl group of an unbranched, aliphatic monocarboxylic acid having from 6 to 24 carbon atoms.

15. The method of claim 13 wherein the acyl group to be introduced is selected from the group comprising $CH_3(CH_2)_8CO$—, $CH_3(CH_2)_{10}CO$—, $CH_3(CH_2)_{12}CO$—, $CH_3(CH_2)_{14}CO$—, $CH_3(CH_2)_{16}CO$—, $CH_3(CH_2)_{18}CO$—, $CH_3(CH_2)_{20}CO$— and $CH_3(CH_2)_{22}CO$—.

16. The method of claim 15 wherein the acyl group to be introduced is $CH_3(CH_2)_{12}CO$—.

17. The method according to claim 1 wherein the acyl group to be introduced is one of the acyl groups of a dicarboxylic acid of the general formula:

HOOC—D—COOH (II)

wherein D is a long chain hydrocarbon group.

18. The method of claim 17 wherein the acyl group to be introduced is one of the acyl groups of a dicarboxylic acid of the general formula (II) wherein D is an unbranched, divalent aliphatic hydrocarbon group having from 6 to 22 carbon atoms.

19. The method of claim 17 wherein the acyl group to be introduced is selected from the group consisting of $HOOC(CH_2)_4CO$—, $HOOC(CH_2)_6CO$—, $HOOC(CH_2)_8CO$—, $HOOC(CH_2)_{10}CO$—, $HOOC(CH_2)_{12}CO$—, $HOOC(CH_2)_{14}CO$—, $HOOC(CH_2)_{16}CO$—, $HOOC(CH_2)_{18}CO$—, $HOOC(CH_2)_{20}CO$— and $HOOC(CH_2)_{22}CO$—.

20. The method according to claim 1 wherein the acyl group to be introduced is a group of the general formula (III):

$CH_3(CH_2)_xCONHCH(COOR^1)CH_2CH_2CO$— (III)

wherein x is an integer from 8 to 24 and $R^1$ is hydrogen or a group which can be exchanged with hydrogen when the acylation has been performed.

21. The method of claim 20, wherein x is 10, 12 or 14.

22. The method of claim 20, wherein $R^1$ is methyl, ethyl or tert-butyl.

23. The method according to claim 1 wherein the acyl group to be introduced is a group of the general formula (IV):

lithocholoyl—$NHCH(COOR^2)CH_2CH_2CO$— (IV)

wherein $R^2$ is hydrogen or a group which can be exchanged with hydrogen when the acylation has been performed.

24. The method of claim 23, wherein $R^2$ is methyl, ethyl or tert-butyl.

25. The method according to claim 1, wherein the activated amide is an azolide of the acid corresponding to the acyl group to be introduced.

26. The method of claim 25, wherein the azolide is derived from an azole selected from the group consisting of pyrazole, imidazole, 1,2,3-triazole, 1,2,4-triazole, tetrazole and phenyltetrazole.

27. The method of claim 25, wherein the azolide is derived from a benzanelated azole.

28. The method of claim 25, wherein the azolide is derived from an azole selected from the group consisting of indazole, benzimidazole and benzotriazole.

29. The method of claim 25, wherein the acylating agent is 1-tetradecanoyl benzotriazole.

30. The method of claim 25, wherein the azolide is derived from a benzotriazole which is mono- or disubstituted with a substituent selected from the group consisting of $C_1$–$C_4$ alkyl, halogen and nitro.

31. The method of claim 30, wherein the azolide is derived from the group consisting of 5-methylbenzotriazole, 5-chlorobenzotriazole, 5-nitrobenzotriazole, 5,6-dimethylbenzotriazole and 5,6-dichlorobenzotriazole.

* * * * *